United States Patent [19]
Micheli

[11] 4,249,156
[45] Feb. 3, 1981

[54] UNCOMPENSATED LOW TEMPERATURE STOICHIOMETRIC AIR/FUEL RATIO EXHAUST GAS SENSOR

[75] Inventor: Adolph L. Micheli, Mt. Clemens, Mich.

[73] Assignee: General Motors Corporation, Detroit, Mich.

[21] Appl. No.: 19,276

[22] Filed: Mar. 9, 1979

[51] Int. Cl.³ .............................................. H01L 7/00
[52] U.S. Cl. ...................................... 338/34; 73/27 R
[58] Field of Search ................... 338/34; 73/27 R, 23; 422/83, 88, 98; 23/232 E; 324/65 P; 264/28; 29/610

[56] References Cited
U.S. PATENT DOCUMENTS

| | | | |
|---|---|---|---|
| 3,479,257 | 11/1969 | Shaver | 338/34 |
| 3,558,280 | 1/1971 | Panson et a. | 73/27 |
| 3,886,785 | 6/1975 | Stadler et al. | 73/27 R |
| 3,893,230 | 7/1975 | Stadler et al. | 23/232 E |
| 3,932,246 | 1/1976 | Stadler et al. | 338/34 X |
| 4,007,435 | 2/1977 | Tien | 338/34 |
| 4,138,881 | 2/1979 | Isenberg | 73/27 R |
| 4,151,503 | 4/1979 | Cermak et al. | 73/27 R X |

*Primary Examiner*—C. L. Albritton
*Attorney, Agent, or Firm*—Robert J. Wallace

[57] ABSTRACT

A titanium oxide resistive-type exhaust gas oxygen sensor having a unique microstructure of interlocked highly irregular, flake-like particles forming a highly durable porous body preferably having a surface area greater than about 3 square meters per gram. A method for producing such particles and forming them into such a high surface area body is also described.

2 Claims, 5 Drawing Figures

4,249,156

UNCOMPENSATED LOW TEMPERATURE STOICHIOMETRIC AIR/FUEL RATIO EXHAUST GAS SENSOR

FIELD OF THE INVENTION

This invention relates to a titanium dioxide resistive-type exhaust gas oxygen sensor. More particularly it concerns an improved titanium dioxide body for such a sensor, and to a method of making the improved body.

BACKGROUND OF THE INVENTION

It is known that the titanium dioxide exhibits a change in electrical resistivity when exposed to a change in oxygen partial pressure. An especially big change in electrical resistivity occurs when the atmosphere changes from oxidizing to reducing. For example, when titanium dioxide is exposed to equilibrated exhaust gases resulting from combustion of a fuel lean air/fuel mixture, the titanium dioxide will exhibit a high resistivity. When exposed to equilibrated exhaust gases resulting from combustion of a fuel rich air/fuel mixture, the titanium dioxide will exhibit a significantly lower resistivity. For this reason, titanium dioxide has previously been used in internal combustion engine exhaust gas oxygen sensors to detect departures in exhaust gas composition from stoichiometry. In sensing such departures, of course, one is indirectly sensing engine intake air/fuel ratio. Such sensing can be used, for example, to regulate a closed loop air/fuel ratio control system for an internal combustion engine.

A complicating factor is that titanium dioxide resistivity also changes as a function of temperature. Further, internal combustion engine exhaust gas temperatures vary widely. Further, the exhaust gases should be equilibrated, or inaccuracies result. Porous titanium diode materials impregnated with oxidation catalysts have been used to reduce such inaccuracies. Nonetheless, at low temperatures resistivity has increased too much. In addition, the more porous bodies used to obtain more rapid equilibration may be relatively soft and questionably durable. Increasing hardness may have required high sintering temperature and corresponding losses in surface area, adversely affecting low temperature performance.

Aggravating the aforementioned problems, is that the amplitude of the exhaust gas temperature variation is increasing. Exhaust gas temperatures in some more recent fuel efficient engines can now stay at much lower levels, both on engine warm-up and at idle after warm-up. There is no titanium dioxide exhaust gas oxygen sensor publically disclosed or commercially available that can be used with such engines without requiring some form of temperature compensation or supplementary heating. Temperature compensation alone may not even be enough, if sensor cycle time at the low temperatures is too slow for the system in which it is used. In such instance, the sensor simply does not control the system at low temperatures. Prior sensors require temperature compensation and/or have controllability problems below 300° C.

I have found how to provide a titanium dioxide sensor that has a sufficiently low resistance at low temperatures that neither temperature compensation nor supplementary heating is required. In addition, I have found how to make the sensor body more durable by a technique in which severe firing is unnecessary. Cycle time is comparable to an existing sensor and response time may even be quicker.

OBJECTS AND SUMMARY OF THE INVENTION

Accordingly, an object of this invention is to provide an improved resistance-type titanium dioxide exhaust gas oxygen sensor.

An additional object of this invention is to provide an improved method of making a resistance-type titanium dioxide exhaust gas oxygen sensor.

The invention comprehends a titanium dioxide resistive-type exhaust gas oxygen sensor having a porous sintered body with a unique microstructure. Extremely fine, interlocked, highly irregular, flake-like particles of titanium dioxide form a highly durable porous body having a surface area greater than about 3 square meters per gram. In making the body, finely divided titanium dioxide particles of an anatase microstructure are precipitated in water. The particles are then separated from the water, dried without significantly changing them or agglomerating them, pressed into a body having high green strength, sintered at a relatively low temperature to provide high mechanical strength without changing particle microstructure from flake-like to granular, whereby a high surface area in the body is preserved. The highly porous and durable body is then impregnated with a platinum group metal catalyst.

BRIEF DESCRIPTION OF THE DRAWING

Other objects, features and advantages of this invention will become more apparent from the following description of preferred examples thereof and from the drawing, in which.

DESCRIPTION OF THE PREFERRED EMBODIMENTS

Figure 1:
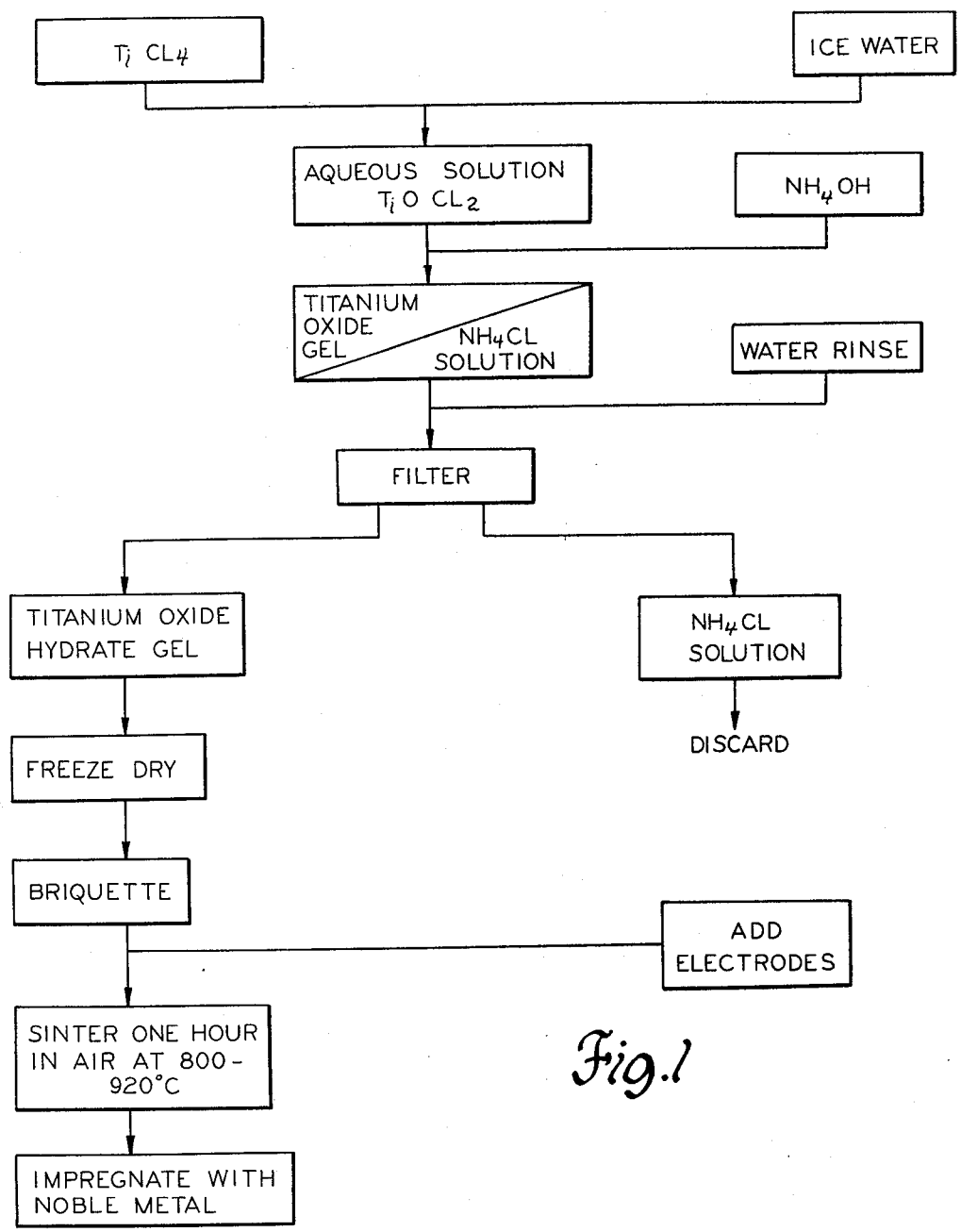
FIG. 1 diagrammatically illustrates the process of the invention.

The low temperature performance, high strength and low temperature sinterability of my sensor are apparently attributable to a unique crystalline structure, a microstructure, of the sensor body. This microstructure is believed to produce a strongly bonded porous body having an unusually high surface area. In making the body, a special form of titanium dioxide is prepared and then specially processed to preserve attributes of that form. The special titanium dioxide is prepared by dissolving titanium tetrachloride in water. Ice water is preferably used, since dissolution of the titanium tetrachloride is a highly exothermic reaction. I believe that an aqueous solution of titanium oxy-chloride ($TiOCl_2$) results. An alkali such as ammonium hydroxide is then added to the solution, to precipitate a hydrated titanium oxide gel. If ammonium hydroxide is used as the precipitating agent the resultant hydrated titanium oxide gel precipitate is dispersed in an ammonium chloride solution as formed. The gel appears to be of extremely fine distinctive anatase titanium dioxide particles. These particles appear to lend linear or polymeric molecular characteristics to the gel that are conducive to a sheet-like or laminar microstructure with high surface area. These are the microstructure characteristics that I wish to preserve in the element body produced in accordance with this invention.

After precipitation, the gel is separated from the ammonium chloride solution by filtering or the like. Filtration through paper by means of a pressure differential can be used, as for example suction or pressure filtration. However, other techniques for mechanically separating the ammonium chloride solution from the precipitate might prove to be useful too, as for example centrifuging. The gel is separated from the ammonium chloride solution without any significant prior treatment that changes the characteristics of the gel particles. For example, the precipitate is not heated or otherwise digested before filtration. After filtration, the gel is thoroughly rinsed with water to substantially remove any residual ammonium chloride. It is essential that no organic solvents be used to rinse the precipitate, and none be added previously to the unfiltered solution to facilitate filtration, as is sometimes customary. It appears that rinsing the precipitate with an alcohol or other organic solvent produces a change in the nature of the precipitate that is not recognizable until later. This change precludes one from obtaining the aforementioned distinctive microstructure in the element body made from these precipitated titanium oxide particles.

The ammonium chloride solution filtered from the gel is discarded. The residue gel is then freeze dried. Freeze drying is essential to obtaining the distinctive element body microstructure of this invention. In freeze drying, the residue is separated from the filter paper used in the aforementioned filtration. The paper may be peeled from the residue, or the residue scraped from the filter paper. In any event, the residue is spread out on a 25 cm.×19 cm.×4 cm. drying tray or pan and liquid nitrogen poured into the tray over it. A quantity of liquid nitrogen is used sufficient to cover the entire residue. This rapidly freezes the entire residue, additionally insuring acquisition of the intended particle structure. The nitrogen is allowed to evaporate. The tray is then placed in a vacuum chamber and the vacuum chamber is evacuated. The pressure in the chamber can be maintained below about 4 Torricelli at a temperature of 70° C. for about 12 hours to freeze dry about 100 grams of titanium oxide hydrate residue gel. Spray freeze drying the filtered or unfiltered gel is not desired, since it produces undesirably large powder agglomerates of lower surface area. The freeze drying described above produces extremely fine crystals of anatase titanium dioxide that appear to retain the polymeric, lamellar, characteristics of the gel. The individual particles are flake-like in characteristic and are the order of 100 angstroms or less across their major faces. They are extremely irregular on their edges, so as to provide a generally digitated flake periphery and extremely high surface area. Nevertheless, these particles do not agglomerate, and produce a very fine fluffy, i.e. friable, powder that need not be ground at all for further processing. Since grinding is unnecessary to prepare the powder for further processing, the characteristics of the particles as originally deposited in the gel are substantially retained. Substantial preservation of particle character is an important part of this invention, as previously mentioned. It should be recognized, however, that once the powder is freeze dried as described above, it may be desirable to subsequently spray dry it to form more flowable agglomerates. Spray drying at the higher temperatures may provide sufficiently high surface area agglomerates if the particles in them were previously freeze dried.

A quantity of the freeze dried powder is then placed in a die to form a circular tablet almost 7 mm. in diameter and 1.3 mm. thick. The powder is pressed at 40,000 pounds per square inch to form the tablet. Satisfactory tablets have been made by pressing the powder at only 5,000 pounds per square inch. However, the higher briquetting pressure appears to provide a product which has a much higher green strength. A briquette pressed at 40,000 psi pressure does not break apart when probed with a needle, and will withstand rough handling such as dropping onto a table top. This powder is also somewhat distinctive in that it withstands the high briquetting pressures of about 40,000 psi without producing a fragile resultant product as many powders do.

As previously indicated, the particles of my powder have an extremely irregular, digitated, periphery. This permits briquetting pressures of only 5,000 psi to be used and still provides adequate tablet strengths both in grain and sintered form. The highly irregular edges on the platelets apparently interlock with each other even at lower briquetting pressures. This interlock apparently permits high briquetting pressures to be used, so that extremely good body strength and hardness can be obtained with only minimal sintering. During the briquetting, the platelets appear to generally orient with their major surfaces perpendicular to the applied pressure and parallel to one another. The result is a generally lamellar, striated or stratified, type of crystalline microstructure in the tablet when viewed under magnification.

Figure 2:
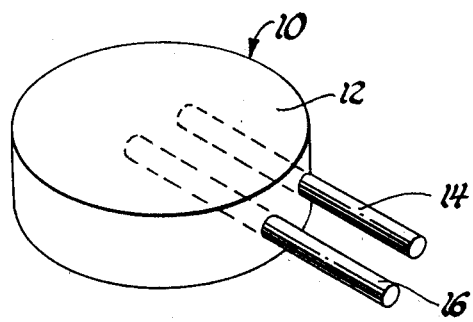
FIG. 2 shows an isometric drawing of a titanium dioxide exhaust gas sensor element.

A tablet formed as hereinbefore described is the body portion 12 of the exhaust gas oxygen sensing element 10 shown in FIG. 2. Except for the aforementioned microstructure uniqueness in body 12, sensor element 10 is generally similar to elements previously suggested in the art. For example, body 12 is a porous titanium oxide tablet. Adjacent ends of two parallel platinum wires 14 and 16 are embedded about 3 mm. into the tablet from its edge. The wires are 0.25 mm. in diameter and are spaced about 1 mm. apart. Platinum wires 14 and 16 serve both as resistance measurement electrodes and as electrical terminals for these electrodes. Body 12 is porous and impregnated with a catalyst for equilibrating exhaust gases to which the element 10 is to be exposed. One or more of the platinum group of metals, such as platinum, palladium, iridium, osmium and rhodium, can be used as a catalyst coating.

Platinum wires 14 and 16 are embedded in body 12 before the body is sintered, so that the sintering operation can also be used to affix the wires in place. In this connection, two spaced parallel holes are drilled in the tablet edge. The holes are of about the same diameter as the platinum wires. One wire end is pressed into each hole.

The tablet is then sintered for a short period of time in air, as for example at 800°–920° C. I appreciate that sintering at slightly higher temperatures may be desirable. However, it is doubtful that I would want to sinter at a temperature above 1,000° C. I only sinter the body 12 long enough to make it able to withstand rough handling and the abrasive effects of an automotive exhaust gas stream. It is not sintered long enough to change the basic character of the crystalline microstructure previously referred to, when the body is viewed under magnification. Sintering somewhat above 900° C. is desirable since such a temperature will also convert the anatase crystal structure to the more stable rutile crystal structure. It appears that such conversion occurs in my material at temperatures above about 830° C. However, I believe that it is surprising that such conversion will occur in only one hour. X-ray analysis I have had conducted indicates that little anatase remains after heating for only one hour at 920° C. It is also surprising to me that the distinctive high surface area microstructure produced by the anatase particles remains after the particles have been converted to a rutile crystal structure. While conversion to the rutile crystal structure is preferred, it is not necessary, particularly if high temperature exhaust gas conditions are not expected. In such sense, the body need only be sintered long enough to provide good mechanical strength but not so long as to significantly reduce the surface area of the body. In general, any sintering equivalent to about 800°–920° C. for one hour in air can be used. Sintering at about 800° C. for one hour will reduce surface area to about 6 square meters per gram. Sintering at about 920° C. for one hour will reduce surface area to about three square meters per gram. Concurrently the platinum wires 14 and 16 bond firmly within body 12.

It should be mentioned that unidirectionally pressing the powder in a die is not the only manner in which the tablet can be formed. It can be produced by isostatic pressing. On the other hand, it might be desired to use a tape-like process in which the powder is temporarily suspended in some form of plastic medium or other temporary binder, formed into a sheet, and then cut into the desired shape. Such shapes can be stacked to form a tablet of desired thickness. Analogously, the platinum wires 14 and 16 could be embedded in the tablet by simply sandwiching them between adjacent stacked shapes. It should also be mentioned that electrodes could be provided on the major faces of the tablet by firing a conductive ink to these major faces. Terminal wires can be soldered to the conductive inks to provide a finished element. Other variations on manufacture of the tablet, application of electrodes, formation of terminal leads, and the like, can no doubt be made. It may even be possible to use my material as a thick film coating on a suitable support, such as an alumina plate. In such instance the coating would be the equivalent of body 12 in FIG. 2. In substance, any of the techniques which would be suitable for making other titanium dioxide sensor elements can also be used in accordance with this invention.

It is believed that the unique microstructure of body 12 provides an extremely high surface area. This high surface area may permit the titanium dioxide to be equilibrated faster and provide a highly effective catalyst support for equilibration of the exhaust gases. It is believed that extensive sintering can destroy this high surface area. Accordingly, in this invention body 12 is sintered only long enough to impart sufficient mechanical strength and durability to the body 12 but not so long as to reduce its surface area substantially below about three square meters per gram. A significantly more extensive sintering tends to change the particle microstructure to globular or spherical, which is more characteristic of the structure obtained by sintering commercially available rutile particles of titanium dioxide. Such particles produce a decidedly lower surface area body than is obtainable with this invention. Further, I believe my material can be sintered at such a low temperature for such a short time because the titanium dioxide particles are so unique. They do not require severe thermal treatment to bond strongly together.

After sintering, the body is impregnated with the catalyst metal. Impregnation can be accomplished by any one of the normal and accepted means, as for example by dipping the sintered body in an aqueous solution of chloroplatinic acid and rhodium chloride in the desired proportions to produce a coating containing 85% by weight platinum and 15% by weight rhodium. The tablet is then heated in a reducing atmosphere, such as forming gas, at 500° C. for one hour and then in air at 800° C. for one hour. This deposits fine particles of rhodium and platinum on the surface of the titanium dioxide particles within the micropores of body 12. It is expected that other catalysts can be used too. It should be understood that any technique which will provide a thorough impregnation of the body with a suitable catalyst can be used. In some instances it may even be desirable to evacuate the body before impregnation to insure the most thorough impregnation.

Figure 3:
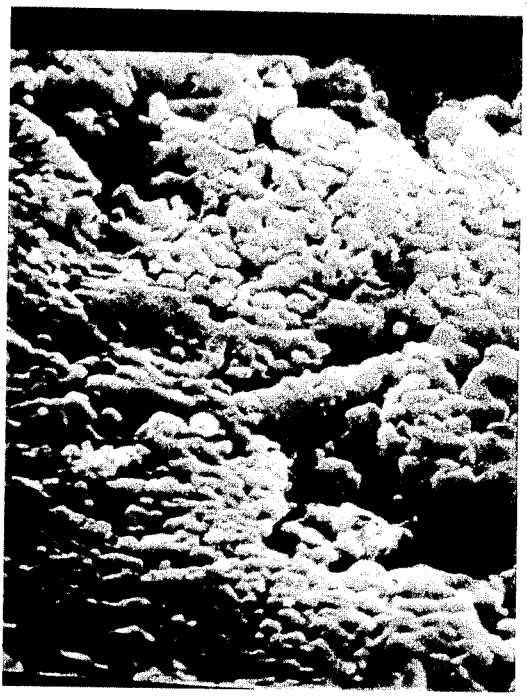
FIG. 3 shows a photomicrograph of a titanium dioxide sensor element material produced in accordance with this invention.

FIG. 3 shows a photomicrograph of a portion of body 12, enlarged 10,000 times, after it has been sintered and before it was coated with the catalyst. As can be seen, the body 12 has a generally striated or laminar appearance, characteristic of the compressed irregular flake-like particles previously referred to. This body was briquetted at 40,000 psi and sintered at 920° C. for one hour in air. It has a surface area of about three square meters per gram.

Figure 4:
FIG. 4 shows a photomicrograph of a commercially available titanium dioxide sensor element body material.

FIG. 4 shows a photomicrograph that is a 10,000 times magnification of a commercially available titanium dioxide resistive type sensor body. As can be seen the crystal structure has a decidedly different appearance in which the particles are larger and more granular in appearance. This body has a catalyst coating. Catalyst particles may be distinguishable on the granular titanium dioxide particles. Uncoated body samples were not available to this inventor. The surface area in this body of FIG. 4 is decidedly smaller than in the body 12 of this invention, shown in FIG. 3. The process by which the body of FIG. 4 was produced is not known by the applicant hereof. However, attention is drawn to FIG. 5, which shows a photomicrograph that also is a 10,000 times magnification. It shows an element body made from commercially available rutile titanium dioxide, briquetted at a pressure of about 5,000 pounds per square inch and sintered at a temperature of approximately 920° C. for one hour in air. As with the FIG. 3 body, it contains no catalyst coating. It is shown without a catalyst coating to better illustrate the titanium dioxide microstructure. It was pressed at only 5,000 psi because significantly higher pressure produced a weaker body. It is to be noted that there is a much greater similarity in crystalline microstructure between FIGS. 4 and 5, than there is between FIGS. 3 and 5. It should also be noted that the sensor elements of FIGS. 4 and 5 were not useful as exhaust gas oxygen sensors below about 300° C. without some form of temperature compensation.

Figure 5:
FIG. 5 shows a photomicrograph of commercial titanium dioxide sensor element body material made with finely ground commercially available rutile titanium dioxide.

When the sensor element is exposed to exhaust gases, the electrical resistivity of the titanium dioxide changes. This provides a change in electrical resistance between the embedded ends of platinum wires 14 and 16. This change in resistance can be conveniently measured by a voltage divider. The sensor element would be placed in series with a reference resistor. One of platinum wires 14 and 16 is connected to an applied voltage and the other to one end of the reference resistor and to a voltage reference terminal. Element resistance can change too much with respect to the reference resistance when temperature changes. If so, changes in resistance due to exhaust gas content changes may no longer be discernable. A constant voltage applied to wire 14 will produce a variable voltage at the voltage reference terminal, depending upon the resistance of body 12. The reference voltage will then provide a signal which is indicative of the oxygen content in the gas to which the sensor element is exposed. For example, elements of FIGS. 4 and 5 provide extremely high resistances below about 350°, as compared to the reference resistor, regardless as to whether or not the sensor element is exposed to an oxidizing or reducing ambient gas. In such instance, one cannot discern whether the ambient gas is rich or lean, unless the reference resistor is changed to a higher value. Analogously, some prior sensors had a resistance at low temperatures that was generally equal to or greater than the lean resistance at higher temperatures. In such event, one had to also include a temperature sensor in the system to identify whether the high resistance was attributable to temperature or lean air/fuel ratios. Changing the resistor and identifying the temperature are forms of temperature compensation that are required. Such compensation, of course, can be avoided by simply keeping the sensor element at higher temperatures, or even at a constant temperature.

It should also be noted that such sensor elements may take an unduly long time to stabilize to changes in gas composition at such low temperatures, such that the output signal does not reach a constant value before the system must act on it. This produces a gradual shift in apparent stoichiometric point from the true stoichiometric point and eventually produces uncontrollability in the system.

My body 12 has a smaller change in resistance with temperature, as compared to sensor elements having microstructures such as shown in FIGS. 4 and 5. It has provided controllability down to 267° C. Hence, it can operate at lower temperatures without compensation. Also, I believe that it will inherently stabilize more quickly than prior sensors of this type do at low temperatures because of its increased surface area.

The embodiments of the invention in which an exclusive property or privilege is claimed are defined as follows:

1. In a resistive-type exhaust gas oxygen sensor exhibiting a significant change in electrical resistance of titanium oxide in response to deviation in exhaust gas content from stoichiometry, the improvement comprising an interlocked, highly irregular flake-like microstructure in the titanium dioxide having a surface area greater than about 3 square meters per gram for enhancing equilibration and more significant electrical resistance change at lower temperatures.

2. In a resistive-type exhaust gas oxygen sensor exhibiting a significant change in electrical resistance of sintered titanium oxide particles as a function of departures in exhaust gas content from stoichiometry, the improvement wherein said particles are generally platelet in character, have a maximum dimension of the order of about 100 angstroms and have a highly irregular periphery that enhances particle interlock, and said particles are interlocked in said body to form a durable highly porous microstructure having a sufficiently large surface area to permit a more significant resistance change to occur at exhaust gas temperatures below 300° C.

* * * * *